United States Patent

Grohe et al.

[11] 4,010,174
[45] Mar. 1, 1977

[54] THIAZOLINONE-(2)-CARBOXYLIC ACID ESTERS AND PROCESS THEREFOR

[75] Inventors: Klaus Grohe, Cologne; Paul-Ernst Frohberger, Leverkusen, both of Germany

[73] Assignee: Bayer Aktiengesellschaft, Leverkusen, Germany

[22] Filed: Sept. 5, 1975

[21] Appl. No.: 610,818

Related U.S. Application Data

[62] Division of Ser. No. 271,104, July 12, 1972, Pat. No. 3,925,400.

[30] Foreign Application Priority Data

July 28, 1971 Germany ............... 2137649

[52] U.S. Cl. ............... 260/306.7 R; 260/306.7 C
[51] Int. Cl.² ............... C07D 277/14
[58] Field of Search ............... 260/306.7 R, 306.7 C

[56] References Cited

UNITED STATES PATENTS 3,925,400  12/1975  Grohe et al. ............... 260/306.7 R

*Primary Examiner*—Richard J. Gallagher
*Attorney, Agent, or Firm*—Burgess, Dinklage & Sprung

[57] ABSTRACT

Thiazolinone-(2)-carboxylic acid esters having the formula:

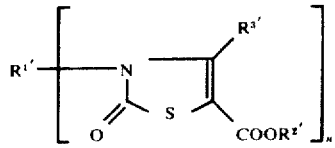

are prepared by reacting a β-amino acrylic acid ester with chlorocarboxyl sulphenyl chloride (COCl-SCl) at a temperature of from 0° to 200° C. The esters are useful as plant protecting agents such as a fungicide.

7 Claims, No Drawings

THIAZOLINONE-(2)-CARBOXYLIC ACID ESTERS AND PROCESS THEREFOR

This is a continuation, of application Ser. No. 271,104, filed July 12, 1972, now U.S. Pat. No. 3,925,400.

BACKGROUND

This invention relates to a process for the production of thiazolinone-(2)-carboxylic acid esters.

It is known that enamino esters of the β-anilino crotonic acid ester type will undergo an intermolecular reaction with $S_2Cl_2$ to give the corresponding disulphide, but will not react by an intramolecular cyclisation to give the corresponding thiazathiole (Ann. 675, 154 (1964)).

SUMMARY

It has now surprisingly been found that thiazolinone-(2)-carboxylic esters having the following general formula:

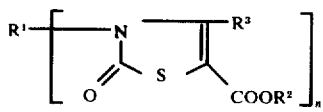
(I)

in which
$n = 1$ or 2 and, where $n = 1$,

R¹ represents a hydrogen atom, an optionally branched $C_1$ to $C_{12}$-alkyl radical or a $C_5$ to $C_6$-cycloalkyl radical, these radicals being optionally substituted by a phenyl radical which may itself be substituted one or more times by fluorine, chlorine or bromine atoms, or by $C_1$ to $C_3$-alkyl radicals; a phenyl radical optionally substituted one or more times by fluorine, chlorine or bromine atoms or by $C_1$ to $C_3$-alkyl groups; or an optionally substituted naphthyl radical; and where $n = 2$, R¹ represents a polymethylene group with from 2 to 6 carbon atoms or a meta- or para-phenylene group.

R² represents an optionally branched $C_1$ to $C_{12}$–alkyl radical or a $C_5$- or $C_6$-cycloalkyl radical, these radicals being optionally substituted by one or more $C_1$ to $C_3$ alkoxy, nitrile or alkoxy carbonyl groups or by a phenyl radical which is itself optionally substituted one or more times by fluorine, chlorine or bromine atoms or $C_1$ to $C_3$-alkyl radicals; and R³ may have one of the meanings listed for R² or represents a hydrogen atom; a lower alkoxy carbonyl group, preferably a methoxy carbonyl or ethoxy carbonyl group; or a phenyl radical optionally substituted one or more times by flourine, chlorine or bromino atoms, or $C_1$ to $C_3$ alkyl groups; or an optionally substituted naphthyl radical, can be obtained by reacting β-amino acrylic acid esters of the general formula:

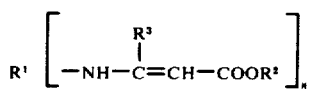
(II)

in which n, R¹, R² and R³ are as defined above, with chlorocarbonyl sulphenyl chloride of the formula:

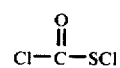
(III)

DESCRIPTION

The β-amino acrylic acid esters which may be used as starting materials are known and can be readily obtained by reacting acyl acetic esters with ammonia or primary aminos, [Organicum, Organisch Chem. Grundpraktikum VEB Deutscher Verlag d. Wissenschaften, Berlin, page 354 (1964); J. Amer. Chem. Soc. 68, 514 (1946)], by reacting Grignard compounds with cyano acetic esters [Collection of Czechoslovak. Chemical Communications 25, 607 (1960)]or by reacting propiolic acid esters or acetylene dicarboxylic esters with ammonia or primary amines [Monatshefte f. Chemie 36, 109 (1915); Chem. Ber. 99, 2526 (1966); Nippon Kagaku Zasshi 82, 632 (1961)].

The following are preferably used in the reaction according to the invention: β-amino crotonic acid methyl ester, β-amino crotonic acid ethyl ester, β-amino crotonic acid-isopropyl ester, β-amino crotonic acid-n-dodecyl ester, β-amino crotonic acid benzyl ester, β-amino crotonic acid cyclohexyl ester, β-amino crotonic acid-β'-phenethyl ester, β-methyl amino crotonic acid ethyl ester, β-anilino crotonic acid ethyl ester, β-benzyl amino crotonic acid ethyl ester, β-[p-chloranilino-]-crotonic acid ethyl ester, β-amino cinnamic acid ethyl ester, β-amino-β-ethyl acrylic acid ethyl ester, β-methyl amino cinnamic acid ethyl ester, α-aminofumaric acid diethyl ester, α-anilino maleic acid diethyl ester, α-m-chloroanilino maleic acid diethyl ester, N,N'-ethylene-bis-[β-amino crotonic acid ethyl ester], N,N'-p-phenylene-bis-[β-amino crotonic acid ethyl ester].

Chlorocarbonyl sulphenyl chloride is also known and readily accessible. It can readily be obtained by reacting trichloromethane sulphenyl chloride with concentrated sulphuric acid (Synthesis 1970, 576).

The reaction of β-amino acrylic acid esters with chlorocarbonyl sulphenyl chloride according to the invention is carried out at temperatures of from 0° to 200° C, preferably from 10° to 150° C.

In general, the β-amino acrylic acid ester and the chlorocarbonyl sulphenyl chloride are heated to between 30° and 200° C, preferably between 30° and 150° C, in a molar ratio of from 1 : 1 to 1 : 2 desirably in an inert solvent, until the evolution of hydrogen chloride stops. In general, the reaction is complete after from 1 to 4 hours.

It is, of course, also possible to combine the hydrogen chloride liberated using one of the bases commonly employed for this purpose, for example pyridine or calcium carbonate.

Suitable inert solvents for use in the process according to the invention include hydrocarbons or chlorinated hydrocarbons such as benzene, toluene, chlorobenzene, o-dichlorobenzene or carbon tetrachloride, tetramethyleusulfom and dioxam are also examples of suitable solvents.

The process according to the invention is illustrated by way of example with reference to the reaction of β-amino crotonic acid ethyl ester and of N,N'-ethylene-bis-[β-amino crotonic acid ethyl ester] with chlorocarbonyl sulphenyl chloride:

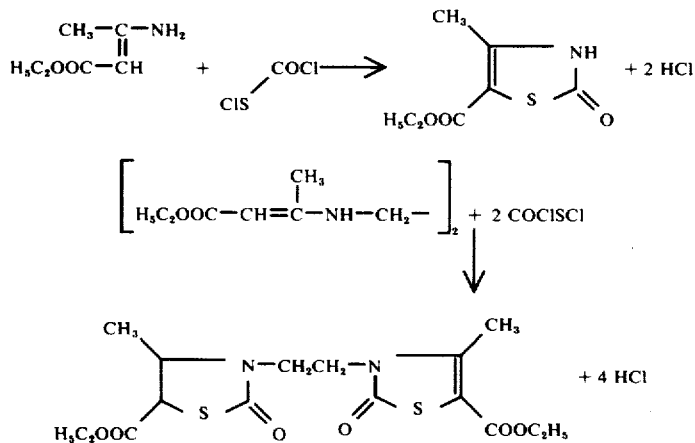

The thiazolinone-(2)-carboxylic acid esters which can be obtained in this way can be readily purified by recrystallisation or by distillation.

In addition to the already known thiazolinone-(2)-carboxylic acid esters which can be obtained in this way, a large number of new thiazolinone-(2)-carboxylic acid esters having the following general formula:

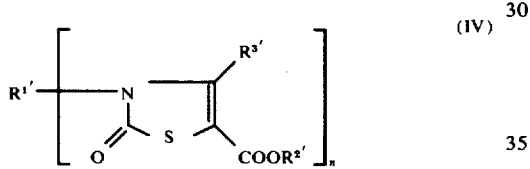

(IV)

in which, n = 1 or 2 and where n = 1
R$^{1\prime}$ represents an optionally branched C$_1$ to C$_{12}$-alkyl radical or C$_5$- or C$_6$-cycloalkyl radical, these radicals being optionally substituted by a phenyl radical which may itself be substituted one or more times by fluorine, chlorine or bromine or by C$_1$ to C$_3$-alkyl radicals; a phenyl radical optionally substituted one or more times by fluorine, chlorine or bromine atoms, or by C$_1$ to C$_3$-alkyl groups; or an optionally substituted naphthyl radical;
and where n = 2
R$^{1\prime}$ represents a polymethylene group with from 2 to 6 carbon atoms or a meta- or para-phenylene group;
R$^{2\prime}$ represents an optionally branched C$_1$ to C$_{12}$-alkyl radical or a C$_5$- or C$_6$-cycloalkyl radical, these radicals being optionally substituted by one or more C$_1$ to C$_3$-alkoxy, nitrile or alkoxy carbonyl groups or by a phenyl radical which is itself optionally substituted one or more times by fluorine, chlorine or bromine atoms or by C$_1$ to C$_3$-alkyl radicals; and
R$^{3\prime}$ may have one of the meanings listed above for R$^{2\prime}$ or represents a hydrogen atom, a lower alkoxy carbonyl group; or a phenyl radical optionally substituted one or more times by fluorine, chlorine or bromine atoms or C$_1$ to C$_3$-alkyl group; or an optionally substituted naphthyl radical
have been made available by this process.

The thiazolinone-(2) carboxylic acid esters of formula (IV) are also new where, if n = 1,
R$^{1\prime}$ represents hydrogen;
R$^{2\prime}$ has the meaning defined above; and
R$^{3\prime}$ represents an alkoxy carbonyl group, preferably a methoxy carbonyl or ethoxy carbonyl group Particularly preferred new compounds are those of the formula (IV)
in which n = 1; and
R$^{1\prime}$ represents an optionally branched C$_1$ to C$_{12}$-alkyl radical or a phenyl radical optionally substituted by one or more fluorine, chlorine or bromine atoms or by C$_1$ to C$_3$-alkyl groups;
R$^{2\prime}$ represents an optionally branched C$_1$ to C$_{12}$-alkyl radical, optionally substituted by a phenyl radical; and
R$^{3\prime}$ has the same meaning as R$^{2\prime}$ or represents a hydrogen atom; a methoxy carbonyl or ethoxy carbonyl group; or a phenyl radical.

The thiazolinone-(2)-carboxylic acid esters are valuable starting materials for the synthesis of plantprotection agents and can also be used as such directly.

Their fungicidal activity is illustrated by way of example with reference to 4-methyl thiazolinone-(2)-carboxylic acid (5)-isopropyl ester and 4-methyl thiazolinone-(2) carboxylic acid-(5)-β-phenethyl ester having the formulae (V) and (VI) respectively:

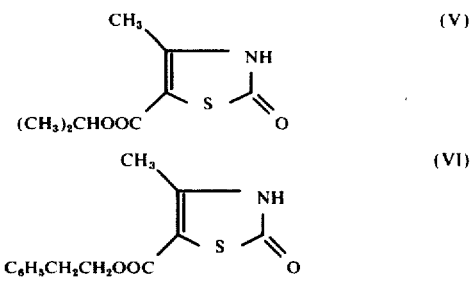

and with reference to 4-methyl thiazolinone-(2)-carboxylic acid-(5)-benzyl ester, 4-methyl thiazolinone-(2)-carboxylic acid (5)-n-butyl ester and 4-methyl thiazolinone-(2)-carboxylic acid-(5)-cyclohexyl ester which have all been found to have good activity in trials.

For example, these compounds can be used as a seed disinfectant to protect wheat from stinking smut, the active material being applied in a quantity of 300 mg/kg of seed. The other new compounds show comparable activity as seed disinfectants.

EXAMPLE 0.5 mol of β-amino acrylic acid ester are added dropwise to 72 g (0.55 mol) of chlorocarbonyl sulphenyl chloride, optionally dissolved in 120 ml of dry chlorobenzene, at from 10° to 20° C. The mixture is then heated to 80° – 90° C for about 1 hour and vigorous evolution of hydrogen chloride takes place. In order to complete the reaction, the reaction mixture is then heated to 120° – 130° C for a further 1 to 2 hours, after which it is worked up either by fractional distillation or by recrystallisation.

Some of the thiazolinone-(2)-carboxylic esters obtained in this way are shown in the following Table:

| | | Thiazolinone-(2)-carboxylic esters of the general formula (I) | | | |
|---|---|---|---|---|---|
| n | $R^1$ | $R^2$ | $R^3$ | mp. (° C) or bp./Torr | Yield (% of theoretical) |
| 1 | $CH_3$ | $C_2H_5$ | $CH_3$ | 62 – 63 | 82 |
| 1 | $C_6H_5CH_2$ | $C_2H_5$ | $CH_3$ | 197 – 199/0.5 | 66 |
| 1 | H | $C_2H_5$ | $CH_3$ | 178 | 75 |
| 1 | H | $(CH_3)_2CH$ | $CH_3$ | 136 | 60 |
| 1 | H | $C_6H_5CH_2CH_2$ | $CH_3$ | 141 | 55 |
| 1 | $C_6H_5$ | $C_2H_5$ | $CH_3$ | 92 – 94 | 75 |
| 1 | $C_6H_5$ | $CH_3$ | $CH_3$ | 139 | 78 |
| 1 | H | $n-C_{12}H_{25}$ | $CH_3$ | 94 | 70 |
| 1 | 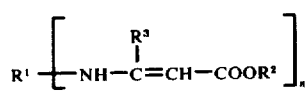 | $C_2H_5$ | $CH_3$ | 92 | 65 |
| 1 | $C_6H_5$ | $C_2H_5$ | $COOC_2H_5$ | 56 – 58 | 74 |
| 2 | $-CH_2CH_2-$ | $CH_3$ | $CH_3$ | 209 | 80 |
| 2 | -C_6H_4- (para) | $C_2H_5$ | $CH_3$ | 307 | 75 |
| 1 | H | $C_6H_5CH_2$ | $CH_3$ | 133 | 70 |
| 1 | H | $n-C_4H_9$ | $CH_3$ | 96 | 78 |
| 1 | H | cyclohexyl | $CH_3$ | 131 | 65 |
| 1 | H | $CH_3$ | $CH_3$ | 212 | 40 |
| 1 | H | $CH_3$ | $CCl_3$ | 128 | 60 |

What is claimed is:

1. Process for producing thiazolinone-(2)-carboxylic acid esters which comprises reacting chlorocarbonyl sulphenyl chloride having the formula COCl—SCl with a β-amino acrylic acid ester having the formula:

$$R^1 \left[ -NH-\underset{\underset{R^3}{|}}{C}=CH-COOR^2 \right]_n$$

wherein, n is 1 or 2 and, when n is 1, $R^1$ is selected from the group of hydrogen, $C_1$ to $C_{12}$-alkyl, $C_5$ to $C_6$-cycloalkyl, the foregoing substituted by phenyl which may itself be substituted one or more times by fluorine, chlorine or bromine atoms or by $C_1$ to $C_3$-alkyl, phenyl, phenyl substituted one or more times by fluorine, chlorine or bromine atoms or by $C_1$ to $C_3$-alkyl, and, when n is 2, $R^1$ is a polymethylene group with from 2 to 6 carbon atoms or a meta- or para-phenylene group;

$R^2$ is selected from the group of $C_1$ to $C_{12}$-alkyl, $C_5$- or $C_6$-cycloalkyl, the foregoing substituted by one or more $C_1$ to $C_3$-alkoxy, nitrile or $C_1$ to $C_3$-alkoxy carbonyl groups or by a phenyl radical which is itself optionally substituted one or more times by fluorine, chlorine or bromine atoms or by $C_1$ to $C_3$-alkyl; and $R^3$ is the same as $R^2$ or is selected from the group of $C_1$-$C_3$-alkoxy carbonyl, phenyl, phenyl substituted one or more times by fluorine, chlorine or bromine atoms or by $C_1$ to $C_3$-alkyl.

2. Process of claim 1 wherein the β-amino acrylic acid ester is selected from the group of β-amino crotonic acid methyl ester,
β-amino crotonic acid ethyl ester,
β-amino crotonic acid benzyl ester,
β-amino crotonic acid cyclohexyl ester,
β-methyl amino crotonic acid ethyl ester,
β-anilino crotonic acid ethyl ester,
β-benzyl amino crotonic acid ethyl ester,
β-amino cinnamic acid ethyl ester,
α-amino fumaric acid diethyl ester,
α-anilino maleic acid diethyl ester, and N,N'-ethylene-bis-[β-amino crotonic acid ethyl ester].

3. Process of claim 1 wherein the reaction is carried out at a temperature of from 0° to 200° C.

4. Process of claim 1 in which the reaction is carried out at a temperature of from 10° to 150° C.

5. Process of claim 1 wherein from 1 to 2 equivalents of chlorocarbonyl sulphenyl chloride are provided per mol of β-amino acrylic acid ester.

6. Process of claim 1 wherein the reaction is carried out in the presence of a solvent.

7. Process of claim 6 wherein the solvent is selected from the group of benzene, toluene, chlorobenzene, o-dichloro-benzene, carbon tetrachloride, sulpholan and dioxan.

* * * * *